United States Patent [19]

Müller et al.

[11] Patent Number: 4,677,221

[45] Date of Patent: Jun. 30, 1987

[54] PROCESS FOR THE PRODUCTION OF THERMALLY COLOR STABLE ALIPHATIC AND/OR CYCLOALIPHATIC DIISOCYANATES AND THE USE THEREOF FOR THE PRODUCTION OF MODIFIED POLYISOCYANATES HAVING IMPROVED COLOR PROPERTIES

[75] Inventors: Hanns P. Müller, Odenthal; Werner Clarenz; Heinrich Grave, both of Bergisch Gladbach, all of Fed. Rep. of Germany

[73] Assignee: Bayer Aktiengesellschaft, Leverkusen, Fed. Rep. of Germany

[21] Appl. No.: 792,376

[22] Filed: Oct. 29, 1985

[30] Foreign Application Priority Data

Nov. 9, 1984 [DE] Fed. Rep. of Germany ....... 3440912

[51] Int. Cl.$^4$ .................... C07C 125/06; C07C 71/00; C08G 18/81
[52] U.S. Cl. .................... 560/115; 560/158; 560/159; 560/332; 528/45
[58] Field of Search .................. 260/453 SP; 560/332, 560/115, 158, 159; 528/45

[56] References Cited

U.S. PATENT DOCUMENTS

| | | | |
|---|---|---|---|
| 2,885,424 | 5/1959 | Spiegler | 260/453 SP |
| 3,183,112 | 5/1965 | Gemassmer et al. | 106/316 |
| 3,799,963 | 3/1974 | Adams | 260/453 |
| 3,873,589 | 3/1975 | Coury et al. | 260/453 |
| 3,903,127 | 9/1975 | Wagner et al. | 260/453 |
| 4,065,362 | 12/1977 | Kayaoka et al. | 260/453 SP |
| 4,386,032 | 5/1983 | Hughes et al. | 260/453 SP |
| 4,388,245 | 6/1983 | Ueyanagi et al. | 260/453 |

FOREIGN PATENT DOCUMENTS 1568623  4/1970  Fed. Rep. of Germany .

*Primary Examiner*—Alan Siegel
*Attorney, Agent, or Firm*—Gene Harsh; Joseph C. Gil; Thomas W. Roy

[57] ABSTRACT

The present invention relates to a process for the production of aliphatic and/or cycloaliphatic diisocyanates which are color stable to heat, which is characterized in that a diisocyanate with aliphatically-and/or cycloaliphatically-bound isocyanate groups is heated in the presence of about 0.1 to 3% by weight, based on the diisocyanate, of at least one compound which is soluble in the diisocyanate and contains at least 3% by weight of structural units corresponding to the formula:

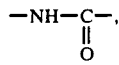

for up to about 5 hours at a temperature of about 100° to 220° C. and the diisocyanate which has been treated in this way is subsequently purified by distillation.

The present invention also relates to the use of the products of the present process for the production of modified polyisocyanates having improved coloration.

6 Claims, No Drawings

PROCESS FOR THE PRODUCTION OF THERMALLY COLOR STABLE ALIPHATIC AND/OR CYCLOALIPHATIC DIISOCYANATES AND THE USE THEREOF FOR THE PRODUCTION OF MODIFIED POLYISOCYANATES HAVING IMPROVED COLOR PROPERTIES

BACKGROUND OF THE INVENTION

1. Field of the Invention

This invention relates to a new process for improving the color stability to heat of aliphatic and/or cycloaliphatic diisocyanates and to the use of the products of this process for the production of modified polyisocyanates, in particular of biuret group-containing polyisocyanates, having reduced inherent color.

2. Description of the Prior Art

Organic polyisocyanates, in particular those having aliphatically- and/or cycloaliphatically-bound isocyanate groups have a wide range of applications in the production of light-stable polyurethane plastics and lacquer coatings having maximum fastness to light, high chalk resistance and excellent gloss.

Modification products of simple aliphatic or cycloaliphatic diisocyanates having reduced vapor pressure are generally used in practice for such applications. These modification products are polyisocyanates containing, for example, allophanate, uretdione, urea, semicarbazide, urethane and, in particular, biuret or isocyanurate structural units and having a reduced vapor pressure. During industrial production of these modification products from the corresponding simple diisocyanates, the inadequate color stability of the reaction mixtures to heat often leads to discolored, usually yellowish to yellow, polyisocyanates.

This yellow coloration frequently has an adverse effect on uniform coloration, in particular when used in the lacquer industry, particularly with pigmented metal effect lacquers.

It has now surprisingly been found that it is possible to overcome these disadvantages by pre-treating the simple diisocyanates used for producing the lacquer polyisocyanates with compounds containing

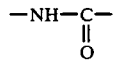

groups. U.S. Pat. No. 4,388,245 describes a process in which modified polyisocyanates, in particular biuret group-containing polyisocyanates, are heated with monomeric diisocyanates and the monomeric diisocyanates are then removed by distillation, but the process in this prior publication cannot be linked with the process according to the present invention, which is described in more detail below, as the process of the U.S. patent relates merely to the conversion of higher functional components in the modified isocyanates to modified polyisocyanates of reduced functionality by heat treatment with monomeric diisocyanates. There is no information about the quality of the monomeric diisocyanate then distilled from modified polyisocyanate in the prior publication. In accordance with the basically different object, quite different proportions of reactants are used in the process according to the prior publication than in accordance with the present invention.

In the conventional process for producing biuret polyisocyanates (see, for example, U.S. Pat No. 3,903,127) the already-formed biuret polyisocyanates are heated in the course of the biuretization reaction in the presence of an excess of monomeric diisocyanates and the excess diisocyanate is subsequently distilled off. However, the quantities used in the known processes are governed by the observation already made in connection with U.S. Pat. No. 4,388,245, namely that the prior art is as little concerned with heating a monomeric diisocyanate with only from 0.1 to 3%, by weight, of biuret polyisocyanate as with achieving the object of the present invention, i.e. improving color stability under heat of the monomeric diisocyanate.

SUMMARY OF THE INVENTION

The present invention relates to a process for the production of aliphatic and/or cycloaliphatic diisocyanates which are color stable to heat, which is characterized in that a diisocyanate with aliphatically- and/or cycloaliphatically-bound isocyanate groups is heated in the presence of about 0.1 to 3% by weight, based on the diisocyanate, of at least one compound which is soluble in the diisocyanate and contains at least 3% by weight of structural units corresponding to the formula:

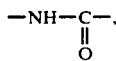

for up to about 5 hours at a temperature of about 100° to 220° C. and the diisocyanate which has been treated in this way is subsequently purified by distillation.

The present invention also relates to the use of the products of the present process for the production of modified polyisocyanates having improved coloration.

DETAILED DESCRIPTION OF THE INVENTION

Starting diisocyanates which are suitable for the process according to the present invention include those corresponding to the following formula:

$$Q(NCO)_2$$

wherein Q represents an aliphatic hydrocarbon radical containing from 2 to 18, preferably from 6 to 10, carbon atoms; a cycloaliphatic hydrocarbon radical containing from 4 to 15, preferably from 5 to 10, carbon atoms; or an aliphatic-cycloaliphatic hydrocarbon radical containing from 6 to 15, preferably from 7 to 12, carbon atoms.

The terms "aliphatic", "cycloaliphatic" and "aliphatic-cycloaliphatic" relate to the type of carbon atoms of the hydrocarbon radicals bonded to the isocyanate groups.

Typical examples of suitable starting isocyanates include aliphatic diisocyanates such as 1,2-diisocyanatoethane, 1,4-diisocyanatobutane, 1,6-diisocyanatohexane, 1,10-diisocyanatodecane or 1,18-diisocyanato-octadecane; cycloaliphatic diisocyanates such as 1,3-diisocyanato-cyclobutane, 1,4-diisocyanato-cyclohexane, 4,4'-diisocyanato-dicyclohexylmethane and mixtures thereof with 2,4'-diisocyanato-dicyclohexylmethane and 3,4'-diisocyanato-4-methyl-dicyclohexylmethane; or aliphatic-cycloaliphatic diisocyanates such as 1-isocyanato-3-isocyanatopropyl-1,3-dimethyl-cyclopentane or 1-isocyanato-3,3,5-trimethyl-5- isocyanatomethyl-cyclohexane (isophorone diisocyanate or IPDI). 1,6-diisocyanatohexane and isophorone diisocyanate are the starting isocyanates most preferably used in the process according to the present invention. 1,6-diisocyanatohexane is particularly preferred. In principle, it is also possible to use mixtures of the exemplified diisocyanates in the process according to the present invention, although this is less beneficial and therefore less preferred.

The diisocyanates to be treated according to the present invention are used in "industrial purity" in the present process. This means that the starting diisocyanates in the process according to the present invention are generally the phosgenation products of the diamines forming the basis of the diisocyanates, worked-up by distillation. The starting diisocyanates generally have a degree of purity of at least 99%.

In the process according to the present invention, the starting diisocyanates are heated in the presence of compounds (hereinafter called "auxiliaries") containing structural units corresponding to the formula:

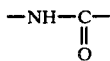

up to about 5, preferably about 1 to 2, hours at about 100° to 220° C., preferably about 150° to 190° C. The suitability of the auxiliaries is conditional on their solubility in the starting diisocyanates to be treated according to the present invention. The structural unit corresponding to the formula

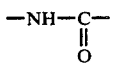

may be part of an allophanate, biuret, urea or urethane group in the auxiliaries. This means that the auxiliaries are allophanate, biuret, urea and/or urethane group-containing compounds. The above-mentioned groupings are present in the auxiliaries in quantities corresponding to an NH—CO group content in the auxiliaries of at least 3%, by weight. The auxiliaries are preferably added to the diisocyanate to be treated. However, it is also possible to produce the auxiliaries in situ by reacting the starting diisocyanate with a compound containing alcoholic hydroxyl groups and/or primary or secondary amino groups so that a proportion of the isocyanate groups in the starting diisocyanate reacts with the added compound to form structural units of the specified type. The quantity of auxiliary or of compound added in situ for forming the auxiliary is calculated in the process according to the present invention such that about 0.1 to 3%, preferably about 0.5 to 2% by weight of the added auxiliary or auxiliary formed in situ are present in the resultant mixture, based on free starting diisocyanate. Suitable auxiliaries to be added to the starting diisocyanates include, for example, (i) ureas which are soluble in the starting diisocyanates, such as urea group-containing reaction products of organic isocyanates, in particular of diisocyanates of the type which are suitable as starting diisocyanates according to the present invention, with primary or secondary amines such as 3,3,5-trimethylcyclohexylamine, dicyclohexylamine, N-methylcyclohexylamine, 3-amino-1,2,4-triazole, stearylamine, methyloctadecylamine, dodecylamine and 1-dodecyl-2,4-diaminobenzene;

(ii) biurets which are soluble in the starting diisocyanates, such as tris-(isocyanatohexyl)biuret or a mixture thereof with its higher homologues or similar biuret polyisocyanates based on other diisocyanates of the type to be used as starting materials according to the present invention;

(iii) urethane group-containing compounds which are soluble in the starting diisocyanates, for example, urethane group-containing reaction products of organic isocyanates, in particular of diisocyanates of the type to be used as starting materials according to the present invention, with mono- and/or poly-hydric alcohols having a molecular weight of 32 to about 2000, preferably 32 to about 200, such as methanol, n-butanol, n-hexanol, ethylene glycol, propylene glycol, diethylene glycol, triethylene glycol, dipropylene glycol, tripropylene glycol and/or oligo- or poly-ester polyols based on dicarboxylic acids such as adipic acid and diols of the type last exemplified;

(iv) allophanates of the type which may be obtained by heating excess quantities of organic isocyanates, in particular of diisocyanates of the type to be used as starting materials according to the present invention, with urethanes of the type listed in (iii).

Auxiliaries which are particularly preferred in the process according to the present invention include biuret group-containing auxiliaries, in particular the biuret polyisocyanates exemplified above under (ii).

Suitable compounds which react in situ with the diisocyanate treated according to the present invention to form suitable auxiliaries according to the present invention include tertiary butanol, dodecylamine, 1-dodecyl-2,4-diaminobenzene, 3-amino-1,2,4-triazole, or alcoholic compounds of the type exemplified above under (iii), but it is necessary to determine in preliminary tests, in each case, whether the auxiliary formed in situ is soluble in the respective starting diisocyanate to be treated.

After the heat treatment according to the present invention, the starting diisocyanate which is present in an excess is recovered by distillation, preferably by vacuum distillation in suitable distillation apparatus. The diisocyanates treated in this way are distinguished from the corresponding diisocyanates not treated according to the present invention by increased color stability under heat. This is particularly important during the conversion of the diisocyanates into higher functional polyisocyanates as the resulting lacquer polyisocyanates. Lacquer polyisocyanates based on diisocyanates not treated according to the present invention have reduced inherent coloration. The products of the present process may be converted to lacquer polyisocyanates, in particular of isocyanurate- or biuret- modified polyisocyanates, using processes known from the prior art. Isocyanurate group-containing polyisocyanates may be produced, for example, according to DE-OS No. 3,033,860, DE-OS No. 3,100,262, DE-OS No. 3,100,263, U.S. Pat. No. 4,324,879 or U.S. Pat. No. 4,288,586. Biuret polyisocyanates may be produced, for example, by reaction of the diisocyanates with a biuretizing agent including aliphatic diamines such as hexamethylene diamine, according to U.S. Pat. Nos. 3,124,605, 3,358,010 or EP-PS No. 3505.

The invention is further illustrated, but is not intended to be limited by the following examples in which all parts and percentages are by weight unless otherwise specified.

EXAMPLE 1

2800 g of 1,6-diisocyanatohexane (HDI) were mixed with 12 g of 3-amino-1,2,4-triazole and heated to 185° C. The aminotriazole reacted to form a solution at from 125°–130° C. The mixture was stirred for 1.5 hours at 185° C. under $N_2$ and the HDI was then distilled off at 165° C. and 20 mm Hg. 2016 g (12 mol) of the HDI pretreated in this way and 148 g (2 mol) of tertiary butanol were mixed and stirred for 10 mins at room temperature under $N_2$. The nitrogen stream was then shut off and the mixture was heated to 185° C. The volume of isobutylene and $CO_2$ evolved was measured using a connected gas meter.

| Time (min) | Temperature (°C.) | Volume (liters) |
| --- | --- | --- |
| 0 | 185 | 20.5 |
| 5 | 185 | 29.0 |
| 10 | 185 | 36.3 |
| 15 | 185 | 42.3 |
| 20 | 185 | 47.7 |
| 25 | 185 | 53.4 |
| 30 | 185 | 58.4 |
| 35 | 185 | 62.3 |
| 40 | 185 | 66.5 |
| 50 | 185 | 73.4 |
| 60 | 185 | 79.2 |
| 70 | 185 | 83.5 |
| 80 | 185 | 87.1 |
| 90 | 185 | 89.3 |

The crude product was cooled and then distilled twice at 160° C. using a thin film evaporator.

A clear, light yellow product having the following characteristics was obtained in this way:

| % NCO | 22.01 |
| --- | --- |
| $\eta$ 25° C. | 6288 mPas |
| HAZEN color index | 100 Apha (according to DIN 53 409) |
| monomer content | 0.5% of free HDI |

EXAMPLE 2

3000 g of HDI were mixed with 30 g of a biuret polyisocyanate based on 1,6-diisocyanatohexane having an NCO content of 22.1%, about 30% of which consisted of tris-(isocyanatohexyl)-biuret and the remainder of the higher homologues thereof, and were stirred for 1.5 hours at 185° C. under $N_2$. The HDI was then distilled off at 165° C. and 20 mm Hg.

2520 g (15 mol) of the HDI pretreated in this way and 185 g (2.5) of tertiary butanol were mixed and stirred for 10 mins at room temperature under nitrogen. The nitrogen stream was then shut off and the mixture was heated to 185° C. The volume of isobutylene and $CO_2$ evolved was measured using a connected gas meter.

| Time (min) | Temperature (°C.) | Volume (liters) |
| --- | --- | --- |
| 0 | 185 | 7.1 |
| 5 | 185 | 15.7 |
| 10 | 185 | 24.7 |
| 15 | 185 | 32.8 |
| 20 | 185 | 40.5 |
| 25 | 185 | 47.5 |
| 30 | 185 | 53.5 |
| 35 | 185 | 59.4 |
| 40 | 185 | 64.3 |
| 50 | 185 | 72.6 |
| 60 | 185 | 81.5 |
| 70 | 185 | 88.9 |
| 80 | 185 | 94.4 |
| 90 | 185 | 99.0 |
| 100 | 185 | 107.0 |
| 110 | 185 | 109.0 |
| 120 | 185 | 111.5 |
| 130 | 185 | 113.0 |

The crude product was cooled, then distilled twice at 160° C. under from 0.2 to 0.4 mm Hg using a thin film evaporator.

A clear, light yellow product having the following characteristics was obtained in this way:

| % NCO | 21.8 |
| --- | --- |
| $\eta$ 25° C. | 9421 mPas |
| HAZEN color index | 90 Apha (according to DIN 53 409) |
| monomer content | 0.21% of free HDI |

COMPARISON EXAMPLE 000 g of industrial HDI were stirred for 1.5 hours at 185° C. under nitrogen. The HDI was then distilled off at 165° C. mm Hg.

520 g (15 mol) of the HDI pretreated in this way and 185 g (2.5 mol) of tertiary butanol were mixed and stirred for 10 mins at room temperature under nitrogen. The nitrogen stream was then shut off and the mixture was heated to 185° C. The volume of isobutylene and $CO_2$ evolved was measured using a connected gas meter.

| Time (min) | Temperature (°C.) | Volume (liters) |
| --- | --- | --- |
| 0 | 185 | 12.5 |
| 5 | 185 | 23.1 |
| 10 | 185 | 33.8 |
| 15 | 185 | 42.5 |
| 20 | 185 | 50.5 |
| 25 | 185 | 57.5 |
| 30 | 185 | 64.9 |
| 35 | 185 | 71.2 |
| 40 | 185 | 76.5 |
| 50 | 185 | 86.5 |
| 60 | 185 | 95.1 |
| 70 | 185 | 101.8 |
| 80 | 185 | 107.4 |
| 90 | 185 | 111.6 |
| 100 | 185 | 112.1 |

The crude product was cooled and then distilled twice at 160° C. under from 0.2 to 0.4 mm Hg using a thin film evaporator.

A clear yellow product having the following characteristics was obtained in this way:

| % NCO | 22.44 |
| --- | --- |
| $\eta$ 25° C. | 6851 mPas |
| HAZEN color index | 520 Apha (according to DIN 53 409) |
| monomer content | 0.16% of free HDI |

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the production of an aliphatic and/or cycloaliphatic diisocyanate which has improved color stability to heat which comprises heating an inductrial diisocyanate containing aliphatically- and/or cycloaliphatically-bound isocyanate groups in the presence of about 0.1 to 3% by weight, based on the diisocyanate, of at least one compound which is soluble in the diisocyanate, contains at least 3% by weight of structural units corresponding to the formula:

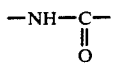

and comprises a biuret ro urea group-containing reaction product of an organic polyisocyanate containing aliphatically- and/or cycloaliphatically-bound isocyanate groups at a temperature of about 100° to 220° C. for a period of up to 5 hours which is sufficient to improve the color stability to heat said diisocyanate and purifying said diisocyanate by distilling off and recovering said diisocyanate.

2. The process according to claim 1 wherein said compound is a biuret group-containing polyisocyanate.

3. The process according to claim 1 wherein said compound is produced in situ by reacting said industrial diisocyanate with a second compound containing primary or secondary amino group(s) so that a proportion of the isocyanate groups in said industrial diisocyanate reacts with the second compound to form said compound containing biuret or urea groups.

4. A process for the production of a biuret-containg polyisocyanate which comprises preparing an aliphatic and/or cycloaliphatic diisocyanate in accordance with the process of claim 1 and subsequently converting said diisocyanate to a lacquer polyisocyanate by reaction with a biuretizing agent.

5. The process of claim 4 wherein said biuretizing agent comprises tertiary butanol.

6. The process of claim 1 wherein said heating is conducted for a period of about 1 to 2 hours.

* * * * *